United States Patent [19]
Boggs et al.

[11] Patent Number: 5,409,465
[45] Date of Patent: Apr. 25, 1995

[54] IMPRESSION SYRINGE

[76] Inventors: Michael S. Boggs, 106 N. Bryan St., Hicksville, Ohio 43526; William Lowry, 8630 Airport Hwy., Holland, Ohio 43528

[21] Appl. No.: 192,596

[22] Filed: Feb. 7, 1994

[51] Int. Cl.⁶ ............................................. A61M 5/00
[52] U.S. Cl. .................................. 604/191; 604/187; 604/43; 604/38
[58] Field of Search ............... 604/187, 43, 191, 38, 604/117

[56] References Cited

U.S. PATENT DOCUMENTS

| | | | |
|---|---|---|---|
| 2,587,984 | 3/1952 | Edwards | 604/38 |
| 3,767,085 | 10/1973 | Cannon et al. | 604/187 |
| 4,014,333 | 3/1977 | McIntyre | 604/43 |
| 4,573,979 | 3/1986 | Blake | 604/43 |
| 4,654,025 | 3/1987 | Cassou et al. | 604/187 |
| 4,655,747 | 4/1987 | Allen, Jr. | 604/191 |
| 4,693,257 | 9/1987 | Markham | 604/187 |
| 4,897,079 | 1/1990 | Zaleski et al. | 604/43 |
| 5,078,691 | 1/1992 | Hamacher | 604/191 |

FOREIGN PATENT DOCUMENTS

| | | | |
|---|---|---|---|
| 2183484 | 6/1987 | United Kingdom | 604/187 |
| 9218177 | 10/1992 | WIPO | 604/187 |

*Primary Examiner*—C. Fred Rosenbaum
*Assistant Examiner*—Perry E. Van Over
*Attorney, Agent, or Firm*—Robert M. Speray

[57] ABSTRACT

An improved syringe having a double walled barrel, a first tip communicating with the interior of the barrel, a plunger slideable within the first tip, and a second tip communicating with the space between the walls of the barrel for delivering a cleansing fluid about the impression material.

12 Claims, 2 Drawing Sheets

IMPRESSION SYRINGE

BACKGROUND

1. Field of the Invention

This invention relates to syringes and is particularly directed to improved syringes for inserting impression material and for simultaneously, cleaning and drying the sulcus.

2. Prior Art

In taking impressions for bridges, crowns and other dental prostheses, it is necessary for the dentist to meticulously clean the sulcus and the area in which the impression is to be taken and to keep this area clear of blood, saliva, etc. while the impression material is inserted. Traditionally, this requires the dentist to hold the syringe, containing the impression material, in one hand and to hold an air hose or the like in the other hand. However, if the dentist needs a free hand, for example, to use a mirror to view the sulcus, it becomes necessary to have someone assist in performing these tasks. This raises the likelihood of inaccuracy due to human error and increases the cost of the procedure to the patient. Numerous prior art devices have been proposed to overcome these problems. However, many of the prior art devices have been bulky and expensive. Other prior art devices have been difficult to sterilize and maintain, while other prior art devices have simply failed to do the job. Thus, none of the prior art devices have been entirely satisfactory.

BRIEF SUMMARY AND OBJECTS OF INVENTION

These disadvantages of the prior art are overcome with the present invention and an improved syringe is provided which is simple and compact in construction and is inexpensive to produce, yet which can easily be sterilized and permits simultaneous and one-handed operation for cleaning and drying of the sulcus and the area in which the impression is to be taken and for delivery of the impression material to the appropriate site.

These advantages are preferably attained by providing an improved syringe having a double walled barrel, a first tip communicating with the interior of the barrel, a plunger slideable within the barrel for delivering impression material through the first tip, and a second tip communicating with the space between the walls of the barrel for delivering a cleansing fluid about the impression material.

Accordingly, it is an object of the present invention to provide an improved syringe.

Another object of the present invention is to provide an improved syringe for delivering impression material to the area in which a dental impression is to be made and for cleaning the sulcus and the surrounding area.

An additional object of the present invention is to provide an improved syringe for delivering impression material to the area in which a dental impression is to be made and for simultaneously cleaning the sulcus and the surrounding area.

A further object of the present invention is to provide an improved syringe which allows delivery of impression material to the area in which a dental impression is to be made and for simultaneously cleaning the sulcus and the surrounding area as a one-handed operation.

Another object of the present invention is to provide an improved syringe which allows one-handed delivery of impression material to the area in which a dental impression is to be made and simultaneously cleaning the sulcus and the surrounding area.

An additional object of the present invention is to provide an improved syringe which is simple and compact in construction, yet which allows one-handed delivery of impression material to the area in which a dental impression is to be made and simultaneously cleaning the sulcus and the surrounding area.

A further object of the present invention is to provide an improved syringe which is simple and compact in construction and is inexpensive to produce, yet which can easily be sterilized and permits simultaneous and one-handed operation for cleaning and drying of the sulcus and the area in which the impression is to be taken and for delivery of the impression material to the appropriate site.

A specific object of the present invention is to provide an improved syringe having a double walled barrel, a first tip communicating with the interior of the barrel, a plunger slideable within the barrel for delivering impression material through the first tip, and a second tip communicating with the space between the walls of the barrel for delivering a cleansing fluid about the impression material.

These and other objects and features of the present invention will be apparent from the following detailed description, taken with reference to the figures of the accompanying drawing.

DETAILED DESCRIPTION OF THE INVENTION

Figure 1:
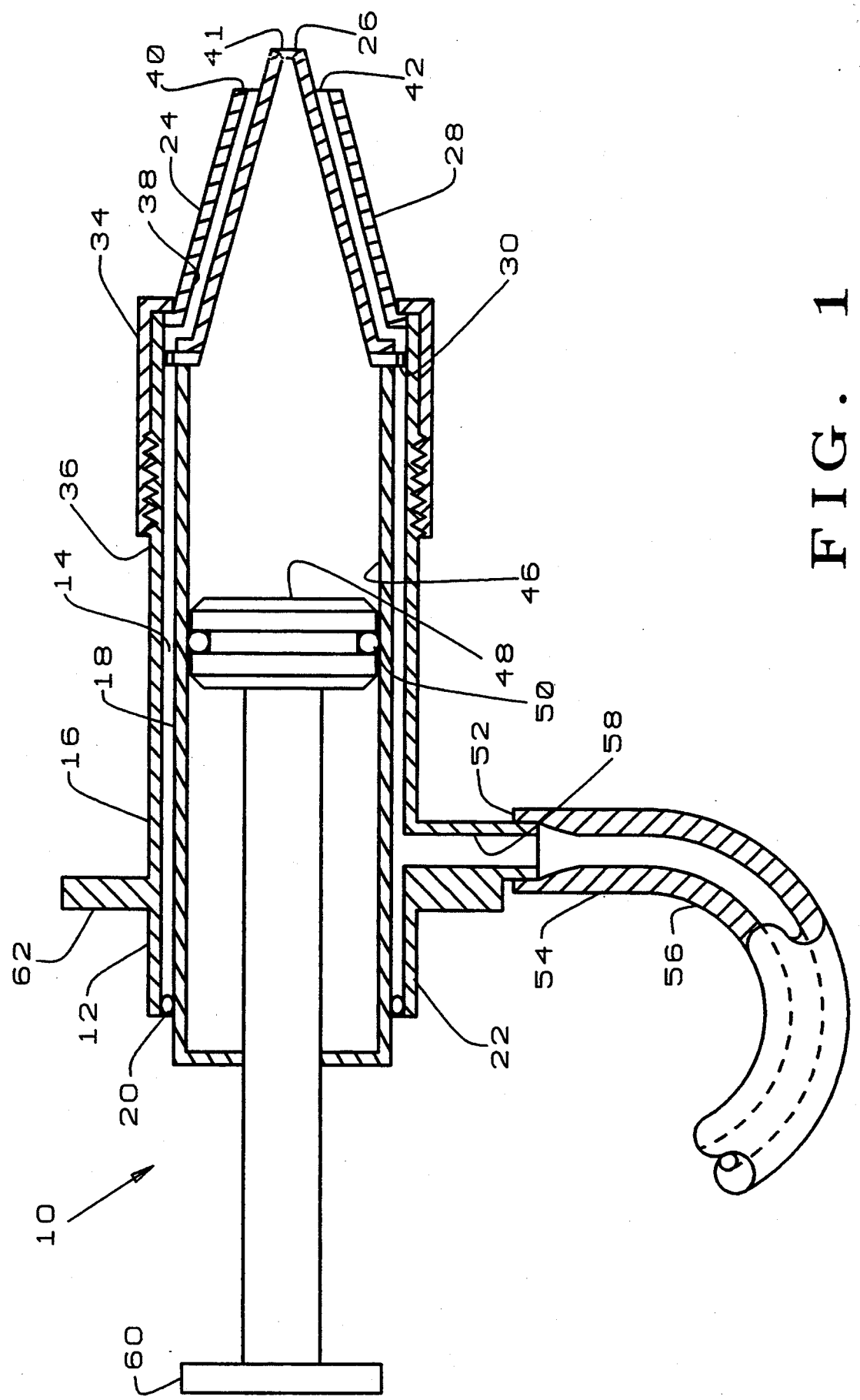
FIG. 1 is a longitudinal section through a syringe embodying the present invention.

In that form of the present invention chosen for purposes of illustration in the drawing, FIG. 1 shows a syringe, indicated generally at 10, comprising a double walled cylinder 12 having an inner annular wall 14 and an outer annular wall 16 separated by an annular space 18. A suitable seal 20 is mounted between the walls 14 and 16, adjacent one end 22 of the syringe 10, to prevent fluids from escaping out of the space 18. Adjacent the opposite end 24 of the syringe 10 are a pair of concentric tips 26 and 28. Tip 26 is mounted on end 30 of the inner wall 14, while outer tip 28 is retained, by a suitable nut 34, to end 36 of the outer wall 16. The outer tip 28 is spaced from the inner tip 26 to provide a channel 38 between the tips 26 and 28 which communicates with the annular space 18 between the walls 14 and 16. The outer tip 28 has an open end 40 and end 42 of inner tip 26 projects beyond end 40 of the outer tip 28 and is formed with an opening 44 which communicates with a central chamber 46 enclosed by inner wall 14. A plunger 48 is slideably mounted within the central chamber 46 and has suitable means, such as O-ring 50, to provide sealing engagement with the wall 14 of the chamber 46. The outer wall 16 is formed with a nipple 52 projecting radially outward adjacent, but spaced from, end 22 of the syringe 10. The external dimensions of the nipple 52 are appropriate to frictionally receive the end 54 of a fluid delivery tube 56 which delivers a desired fluid, such as water, air or a suitable gas, from a supply source, not shown. The nipple 52 is formed with an axial channel 58 which communicates with the space 18 between the inner wall 14 and the outer wall 16. If desired, a drive handle 60 may be provided on the outer end of the plunger 48 and a finger grip 62 may be project outwardly from the outer wall 16 to facilitate one-handed gripping and operation of the syringe 10.

In use, the plunger 48 is removed from the central chamber 46 and the chamber 46 is filled with a desired quantity of material for forming a dental impression. Thereafter, the plunger 48 is reinserted into the chamber 46 and the user grips the syringe 10 by placing his index finger and middle finger on opposite sides of the syringe 10 just forward of the finger grip 62 and places his thumb on the drive handle 60 of the plunger 46. When the fluid delivery hose 56 has been connected to the nipple 52, the fluid flow is turned on and the cleansing fluid flows through channel 58 of nipple 52 into the annular space 18 between the walls 14 and 16 and, thence, flows forward through channel 38 between inner tip 26 and outer tip 28 and is then discharged, through open end 40 of tip 28, to cleanse and dry the sulcus and to drive blood, saliva and debris away from the impression area. When appropriate, the user presses his thumb against the drive handle 60 to force the plunger 46 forward and to extrude the impression material through opening 44 of tip 28 for delivery to the impression area. Because the flow of cleansing fluid surrounds the flow of impression material, it gives the user a clear and unobstructed view of the sulcus and the impression area. This permits greater accuracy in placing the impression material and ensures that the area will be kept clean and free from blood, saliva or debris.

Alternatively, it will be seen that the syringe 10 can be used to accomplish the sterile removal of debris or other undesired material. To accomplish this, plunger 48 would be advanced to its forwardmost position and a suitable fluid can be delivered through hose 56, channel 58 of nipple 52, annular space 18, channel 38 and opening 40 of outer tip 28. Meanwhile, by drawing plunger 48 rearward, a vacuum would be created at opening 44 of inner tip 26, causing atmospheric pressure to force the debris or other unwanted material to be suctioned through opening 44 of inner tip 26 for collection in chamber 46.

Figure 2:
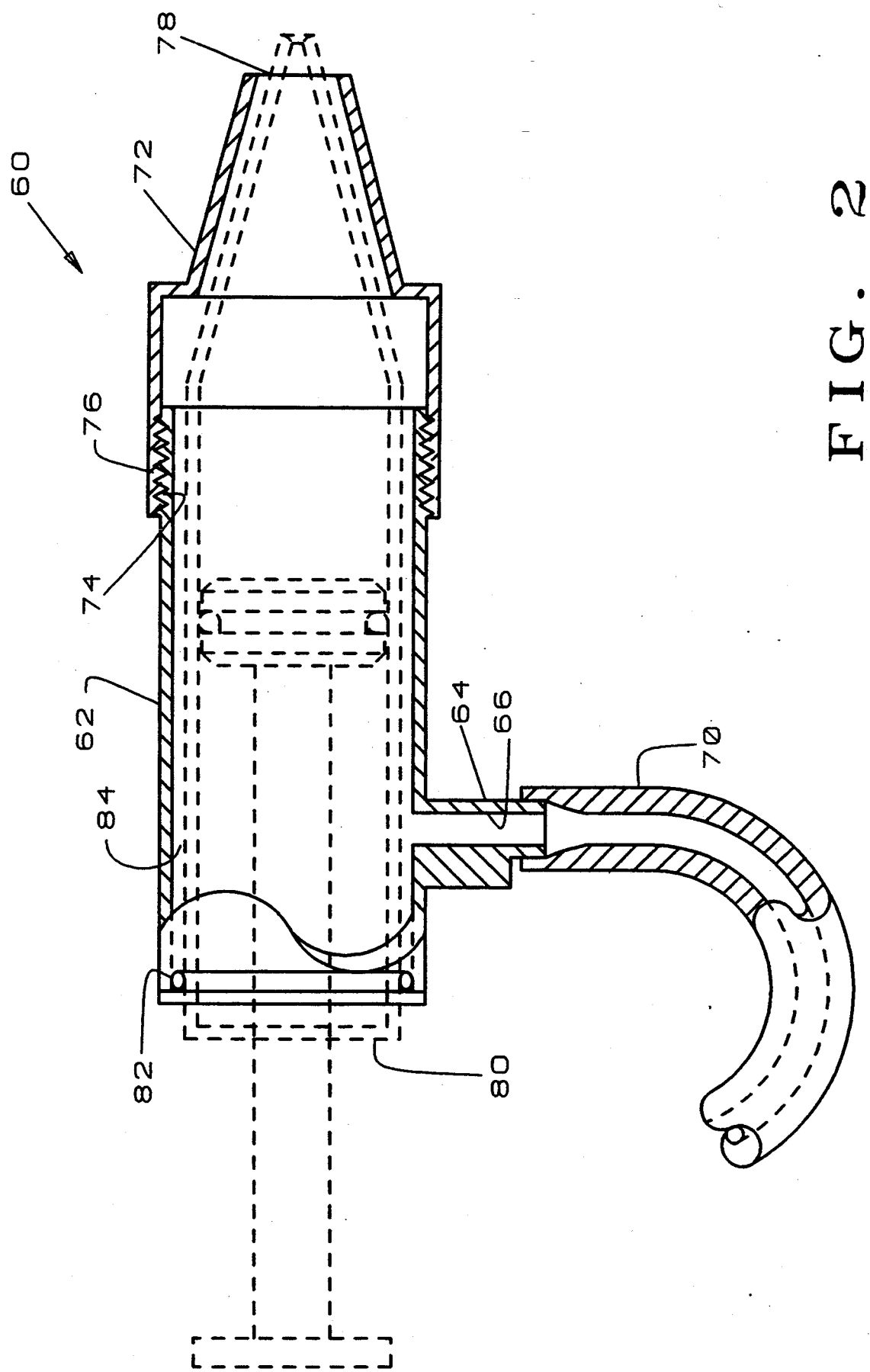
FIG. 2 is a longitudinal section through an alternative form of the syringe of FIG. 1.

FIG. 2 shows an alternative form, indicated generally at 60, of the syringe 10 of FIG. 1. In this form of the present invention, a sleeve 62 is provided having a nipple 64 formed with a channel 66 extending through the nipple 64 and dimensioned to frictionally receive end 68 of a fluid delivery tube 70. A tip 72 is threadedly connected to end 74 of the sleeve 62, as seen at 76 and has an opening 78 at the forward end of the tip 72. The sleeve 62 is dimensioned to slideably receive a conventional syringe 80, shown in dashed lines, and suitable means 82, such as a ring seal or O-ring, is mounted internally of the sleeve 62 and serves to provide a fluid seal between the interior of the sleeve 62 and the exterior of the syringe 80 and also serves to provide a fluid passage 84 between the exterior of the syringe 80 and the interior of the sleeve 62, corresponding to annular space 18 of the syringe 10 of FIG. 1.

By inserting the conventional syringe 80 into sleeve 62, as described above, the sleeve 62 serves to convert the conventional syringe 80 into a double-walled syringe, corresponding to the syringe 10 of FIG. 1, and which can be used to perform substantially the same functions as the syringe 10 of FIG. 1.

Obviously, numerous other variations and modifications can be made without departing from the spirit of the present invention. Therefore, it should be clearly understood that the form of the present invention described above and shown in the accompanying drawing is illustrative only and is not intended to limit the scope of the present invention.

What is claimed is:

1. A syringe comprising:
a double-walled barrel having a space between the walls of said barrel,
a first generally conical tip opening to the interior of said barrel,
a plunger slideable within said interior of said barrel for delivering impression material for discharge through said first tip,
a second generally conical tip communicating with said space between said walls of said barrel.

2. The syringe of claim 1 wherein:
said second tip is concentric with and spaced from said first tip.

3. The syringe of claim 1 wherein:
said second tip delivers said fluid surrounding said impression material discharged through said first tip.

4. The syringe of claim 1 further comprising:
a nipple projecting outwardly from the outer wall of said barrel dimensioned to frictionally receive a fluid supply hose and communicating with said space between said walls to deliver fluid into said space.

5. The syringe of claim 1 further comprising:
a nut releasably securing said first tip to one end of the inner wall of said barrel.

6. The syringe of claim 1 further comprising:
a fluid seal closing the end of said space between said walls opposite from said tips.

7. The syringe of claim 1 wherein:
said first tip is mounted on one end of the inner wall of said barrel.

8. The syringe of claim 1 wherein:
said second tip is mounted on one end of the outer wall of said barrel.

9. The syringe of claim 1 wherein:
said double-walled barrel comprises a sleeve dimensional dimensioned to receive a conventional syringe and having sealing means forming a fluid seal between said sleeve and said conventional syringe and serving to provide a fluid passage between said sleeve and said conventional syringe,
said first tip and said plunger being components of said conventional syringe and said second tip being mounted on said sleeve and encircling said first tip.

10. The device of claim 9 further comprising:
fluid supply means connected to deliver fluid to said fluid passage for discharge through said second tip.

11. The syringe of claim 9 further comprising:
a nipple projecting outwardly from said sleeve and dimensioned to frictionally receive a fluid supply hose and communicating with said fluid passage to deliver fluid into said fluid passage.

12. The syringe of claim 1 wherein:
said plunger is operable to create a vacuum at said first tip to facilitate suctioning of material through said first tip.

* * * * *